United States Patent [19]

Madsen

[11] 4,148,214
[45] Apr. 10, 1979

[54] APPARATUS FOR MEASURING THE VISCOSITY OR CONSISTENCY OF FLUIDS

[75] Inventor: Rud F. Madsen, Nakskov, Denmark

[73] Assignee: Aktieselskabet de Danske Sukkerfabrikker, Copenhagen, Denmark

[21] Appl. No.: 857,452

[22] Filed: Dec. 5, 1977

[30] Foreign Application Priority Data

Dec. 7, 1976 [DK] Denmark .............................. 5496/76

[51] Int. Cl.² ............................................ G01N 11/10
[52] U.S. Cl. ............................................. 73/54; 73/59
[58] Field of Search ....................... 73/54, 59, 53, 55

[56] References Cited

U.S. PATENT DOCUMENTS

| 1,331,861 | 2/1920 | Callan | 73/59 |
| 2,339,991 | 1/1944 | Hagy | 73/55 |
| 3,777,549 | 12/1973 | Lodge | 73/53 |

Primary Examiner—Richard C. Queisser
Assistant Examiner—Joseph W. Roskos
Attorney, Agent, or Firm—Watson, Cole, Grindle & Watson

[57] ABSTRACT

An apparatus for measuring the viscosity or consistency of fluids, such as liquids, emulsions and suspensions, comprises a hydraulic pressure sensor, such as a pressure transducer, and an impeller rotating in front of the sensor so as to produce a periodically varying flow of fluid in a direction towards the sensor.

6 Claims, 4 Drawing Figures

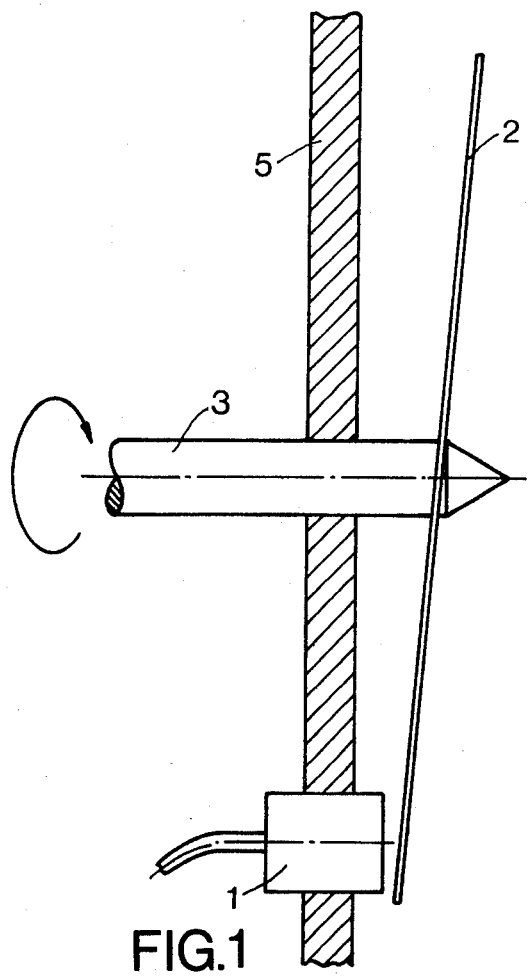
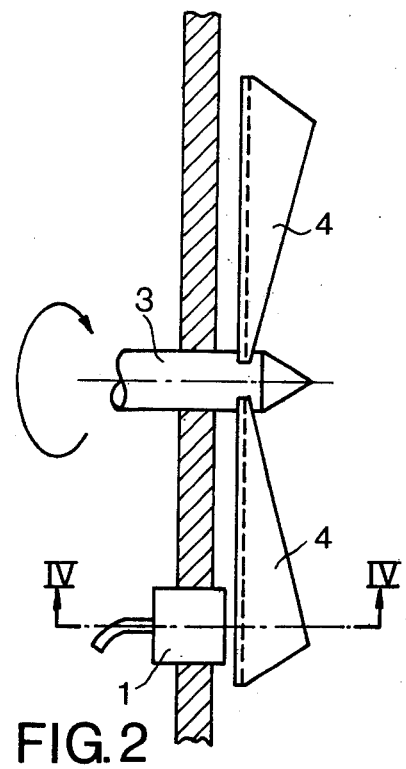
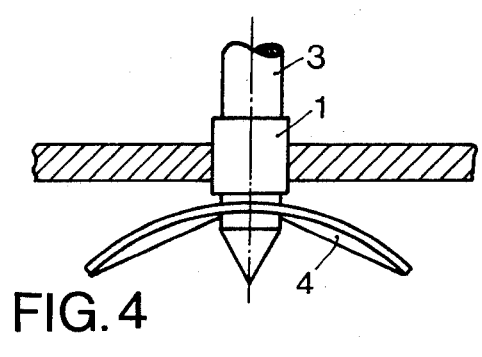
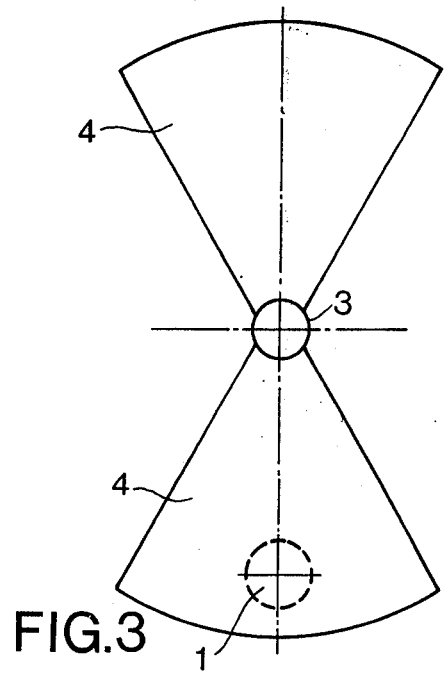
FIG. 1
FIG. 2
FIG. 3
FIG. 4

APPARATUS FOR MEASURING THE VISCOSITY OR CONSISTENCY OF FLUIDS

BACKGROUND OF THE INVENTION

The invention relates to an apparatus for measuring the viscosity or consistency of fluids, such as liquids, emulsions and suspensions.

In open containers the measuring of viscosity or consistency usually does not involve problems. According to one known method a rotating or oscillating first element and a second element mounted on a shaft which is rotatable from a predetermined position against a biasing torque are so placed in the fluid that a viscous coupling is established between them through the liquid, and the torque thereby transmitted to the second element is measured. An example of such a method is known from the U.K. patent specification No. 970,293.

If using a similar method for the measuring of viscosity or consistency of fluids in closed containers, the difficulty arises that either the measurement of torque will include the friction in a stuffing box, which may give rise to considerable errors, or some special means such as a diaphragm or bellows system must be used for transmitting the measurement of the torque from the second element out of the container. By the use of such systems the measurement may be subjected to the influence of pressure and temperature. Besides, for carrying out the measuring according to such a system relatively complicated equipment will frequently be required.

SUMMARY OF THE INVENTION

According to the invention, an apparatus for measuring the viscosity or consistency of fluids, such as liquids, emulsions and suspensions, comprises a hydraulic pressure sensor having a sensing area located in the fluid, and an impelling element which is likewise located in the fluid and is so shaped and subjected to movement in such a manner as to produce a periodically varying flow of fluid in a direction towards the sensing area of the pressure sensor, thereby subjecting the pressure sensor to periodical pressure variations, which can be measured in known manner.

By the present system the advantage is obtained that the measurement will practically exclusively depend on periodic variations of hydraulic pressure, which are produced in a controlled manner, while any influence from other factors, such as pressure and temperature, are, so to speak, filtered off. Such hydraulic pressure variations, as picked up by a hydraulic pressure sensor, can easily be directly measured outside the container.

Since it is the variations of the hydraulic pressure at the sensing area of the sensor that is measured, a method of measuring must be used which is fast enough to respond to these variations. As an expression of the viscosity or consistency of the fluid one may use, e.g., the maximum change of pressure resulting from the movement of the impelling element, or the integral of the change of pressure.

With particular advantage, the impelling element may consist of a rotating body. This is from a constructional point of view the simplest embodiment, although in principle it would also be possible to use an oscillating or reciprocating movement.

In one preferred embodiment of the invention, the impelling element comprises a disk which is fixed to a rotating shaft at an inclination to a plane perpendicular to the axis of the shaft. This embodiment is very simple from a constructional point of view. When the shaft rotates, the disk performs a wobbling movement, thereby creating periodic flow variations which can best be utilized by arranging the sensing area of the sensor in a position slightly within the periphery of the disk at a short distance from the closest position of the disk.

In another preferred embodiment of the invention, the impelling element comprises one or more impeller arms mounted on a rotating shaft. These impeller arms may advantgeously have a U-shaped cross section with the bottom of the U on the side of the impeller facing the sensing area of the pressure sensor. Whether one or the other of these two embodiments will be preferred in a particular case depends mainly on the viscosity range or (for suspensions) the particle range within which the measurement is to be taken.

The measuring of the pressure may on principle be performed by any method which is fast enough. In a particularly advantageous embodiment the hydraulic pressure sensor is an electricl pressure transducer. This may be placed altogether inside the container in which the measurement is undertaken, or in the wall of the container, or it may be placed outside the container and be connected to the interior of the container through a pipe, the mouth of which will then constitute the sensing area.

BRIEF DESCRIPTION OF THE DRAWING

FIG. 1 shows diagrammatically an axial section through one form of an apparatus according to the invention, as mounted in the wall of a container.

FIG. 2 is a corresponding section through another embodiment.

FIG. 3 shows the apparatus of FIG. 2 as seen from the interior of the container.

FIG. 4 is a section along the line IV—IV in FIG. 2.

DESCRIPTION OF THE PREFERRED EMBODIMENTS

In the embodiment shown in FIG. 1, an electrical pressure transducer 1 is mounted in the wall 5 of a container in such a manner that its diaphragm constituting its sensing area is located slightly advanced from the inner face of the wall 5. However, the diaphragm might also be flush with the inner face of the wall. As an impelling element a rotating body is used in the form of a disk 2, which is fixed to a shaft 3 in an inclined position. When the shaft 3 rotates, the disk 2 will therefore perform a wobbling movement so that the edge portion at any time moving past the pressure sensor 1 will move back and forth in front of the sensing area of the sensor and will thereby create a periodically varying flow of fluid in a direction towards the sensing area.

The disk may be perforated between the shaft and the zone which moves past the transducer 1. Hereby the danger of cavitation in the zone of the transducer is reduced, and if there is a vacuum in the container any air that may be sucked in through the stuffing box or other seal between the shaft 3 and the wall 5 will have a possibility of passing through these holes and will therefore have less influence on the measurement.

In the embodiment shown in FIGS. 2, 3 and 4, two impeller arms 4 are mounted on the shaft 3. The impeller arms 4 are U-shaped with the bottom of the U on the side of the impeller arm facing the diaphragm of the pressure transducer 1. Instead of two impeller arms a single impeller arm or a number greater than two may be used. When the shaft rotates, the distance between the pressure transducer and each of the impeller arms will gradually decrease, pass through a minimum and then again gradually increase, whereby a periodically varying flow of fluid in a direction towards the diaphragm of the transducer 1 is produced.

The embodiment of FIGS. 2, 3 and 4 has been found particularly suitable for measuring the consistency of the crystal slurry in the crystallization of sugar in vacuum apparatus. Suitable values of the parameters of the apparatus for this use have been found to be as follows:

RPM of the shaft: 200–600.

Distance between the transducer and the closest zone of the impeller: 1.5 – 4 mm.

Outer diameter of impeller: 150–250 mm.

In order to obtain accuracy of the measurement the RPM should be kept as constant as possible.

Viscosity measuring apparatus of this type will, depending on their construction, have a certain minimum viscosity that will still be measurable because under a certain viscosity the flow becomes turbulent. An apparatus constucted in accordance with the data above specified has been found to be operable from about 10 cp to 100,000 cp.

I claim:

1. An apparatus for determining the viscosity or consistency of fluids, such as liquids, emulsions and suspensions, comprising a hydraulic pressure sensor means having a sensing area located in the fluid, and an impelling element which is likewise located in the fluid and is so shaped and subjected to movement in such a manner as to produce a periodically varying flow of fluid in a direction towards said sensing area of said pressure sensor means, thereby subjecting said pressure sensor means to periodical pressure variations, which are representative of the viscosity or consistency of the fluid.

2. An apparatus as in claim 1, in which said impelling element consists of a rotating body.

3. An apparatus as in claim 1 in which the impelling element comprises a disk which is fixed to a rotating shaft at an inclination to a plane perpendicular to the axis of the shaft.

4. An apparatus as in claim 1, in which the impelling element includes at least one impeller are mounted on a rotating shaft.

5. An apparatus as in claim 4, in which the impeller arms have a U-shaped cross section with the bottom of the U on the side of the impelling element facing said sensing area of said pressure sensor means.

6. An apparatus as in claim 1, in which said pressure sensor means is an electrical pressure transducer.

* * * * *